US012758622B2

(12) United States Patent
Locksley et al.

(10) Patent No.: US 12,758,622 B2
(45) Date of Patent: Oct. 13, 2026

(54) CHITINASE ADMINISTRATION TO THE AIRWAY TO TREAT INFLAMMATION AND AGE-RELATED PULMONARY FIBROSIS

(71) Applicant: The Regents of the University of California, Oakland, CA (US)

(72) Inventors: Richard Locksley, San Francisco, CA (US); Steven Van Dyken, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/604,979

(22) PCT Filed: Apr. 11, 2018

(86) PCT No.: PCT/US2018/027111
§ 371 (c)(1),
(2) Date: Oct. 11, 2019

(87) PCT Pub. No.: WO2018/191379
PCT Pub. Date: Oct. 18, 2018

(65) Prior Publication Data

US 2021/0128698 A1 May 6, 2021

Related U.S. Application Data

(60) Provisional application No. 62/484,394, filed on Apr. 11, 2017.

(51) Int. Cl.
*A61K 38/47* (2006.01)
*A61K 9/00* (2006.01)
(Continued)

(52) U.S. Cl.
CPC .............. *A61K 38/47* (2013.01); *A61P 11/00* (2018.01); *C12Q 1/34* (2013.01); *G01N 33/6893* (2013.01);
(Continued)

(58) Field of Classification Search
CPC .. C12Q 1/34; G01N 33/6893; G01N 2800/12; G01N 2333/924; A61K 38/47;
(Continued)

(56) References Cited

U.S. PATENT DOCUMENTS 5,618,786 A 4/1997 Roosdorp et al.
8,268,306 B2 * 9/2012 Campos .................. A61P 31/04 424/94.61
(Continued)

FOREIGN PATENT DOCUMENTS

CN 106370856 A 2/2017
WO 2002/043695 A2 6/2002
(Continued)

OTHER PUBLICATIONS

WebMD entry to "Nebulizer". Internet Archive, Apr. 10, 2016. (Year: 2016).*
(Continued)

*Primary Examiner* — Sean C. Barron
(74) *Attorney, Agent, or Firm* — MARSHALL, GERSTEIN & BORUN LLP

(57) ABSTRACT

Herein is demonstrated that expression of the enzyme chitinase in the lungs of animals is protective against adverse chitin-mediated inflammation and that with impaired chitinase expression, various inflammatory pathways are enhanced, contributing to conditions such as fibrotic lung disease. Further, it is shown that the prevention and treatment of pulmonary fibrosis and other improvements to lung health are achieved by administration of chitinase to the
(Continued)

lungs. Additionally, methods of assessing chitinase activity in the lungs provide a novel diagnostic measure of lung health.

6 Claims, 3 Drawing Sheets

(51) Int. Cl.
*A61P 11/00* (2006.01)
*C12N 9/42* (2006.01)
*C12Q 1/34* (2006.01)
*G01N 33/68* (2006.01)

(52) U.S. Cl.
CPC .......... *A61K 9/0075* (2013.01); *A61K 9/0078* (2013.01); *A61K 9/008* (2013.01); *C12N 9/2442* (2013.01); *C12Y 302/01014* (2013.01); *G01N 2333/924* (2013.01); *G01N 2800/12* (2013.01)

(58) Field of Classification Search
CPC .... A61K 9/008; A61K 9/0078; A61K 9/0075; A61P 11/00; C12N 9/2442; C12Y 302/01014
See application file for complete search history.

(56) References Cited

U.S. PATENT DOCUMENTS

| | | | | |
|---|---|---|---|---|
| 9,554,993 | B2 | 1/2017 | Tarara et al. | |
| 2013/0136751 | A1 | 5/2013 | Zhu et al. | |
| 2013/0156750 | A1 * | 6/2013 | Elias | C12Q 1/34 435/7.92 |
| 2021/0128698 | A1 | 5/2021 | Locksley et al. | |

FOREIGN PATENT DOCUMENTS

| | | | |
|---|---|---|---|
| WO | 2004092404 | A2 | 10/2004 |
| WO | 2008/002548 | A2 | 1/2008 |
| WO | 2009097262 | A2 | 8/2009 |
| WO | 2018/191379 | A2 | 10/2018 |

OTHER PUBLICATIONS

ExPASy entry to chitinase. Internet Archive, Mar. 6, 2016. (Year: 2016).*
Zhou et al. Chitinase 3-like 1 Suppresses Injury and Promotes Fibroproliferative Responses in Mammalian Lung Fibrosis. Science Translational Medicine (2014), 6(240), 240ra76, 14 pages. (Year: 2014).*
Bucolo et al. Acidic mammalian chitinase and the eye: implications for ocular inflammatory diseases. Frontiers in Pharmacology (2011), 2(43), 4 pages. (Year: 2011).*
Choi et al. House Dust Mite-Derived Chitin Enhances Th2 Cell Response to Inhaled Allergens, Mainly via a TNF-α-Dependent Pathway. Allergy Asthma Immunol Res. (2016), 8(4), 362-374. (Year: 2016).*
Elmonem et al. Immunomodulatory Effects of Chitotriosidase Enzyme. Enzyme Research (2016), article ID 2682680, 9 pages. (Year: 2016).*
UniProtKB entry to Brugua malayi chitinase (P2030).*
Caplan-Shaw et al. Lung Pathologic Findings in a Local Residential and Working Community Exposed to World Trade Center Dust, Gas, and Fumes. JOEM (2011), 53(9), 981-991. (Year: 2011).*
Raghu et al. Incidence and Prevalence of Idiopathic Pulmonary Fibrosis. Am J Respir Crit Care Med (2006), 174, 810-816. (Year: 2006).*
Fitz et al (2012), "Acidic mammalian chitinase is not a critical target for allergic airway disease," Am. J. Respir. Cell Mol. Biol. 46, 71-79.).
Cho, Soo Jung et al., "Chitotriosidase is a biomarker for the resistance to World Trade Center lung injury in New York City firefighters", Journal of Clinical Immunology, 2013, vol. 33, No. 6, pp. 11-34-1142. See pp. 1134, 1135, 1138, 1140; and Table III.
Lee, Chun Geun et al., "Chitinase 1 is a biomarker for and therapeutic target in scleroderma associated interstitial lung disease that augments TGF-β1 signaling", The Journal of Immunology, 2012, 1201115, internal pp. 1-10. See Internal pp. 1-7; and figures 1,2, 4, 5.
VanDyken, Steven J., et al., Spontaneous chitin accumulation in airways and age-related fibrotic lung disease, Cell. Apr. 20, 2017. vol. 169, No. 3, pp. 497-509, and e1-e13. See summary; p. 501; and figures 1-3, 5.
Craig and Scott, 2014, Helminths in the lungs, Parasite Immunology 36:463-474.
Cong et al., "IL-17A-producting T cells exacerbate fine particulate matter-induced lung inflammation and fibrosis by inhibiting PI3K/Akt/mTOR-mediated autophagy," J Cell Mol Med 24:8532-8544 (2020).
Gasse et al., "IL-1 and IL-23 Mediate Early IL-17A Production in Pulmonary Inflammation Leading to Late Fibrosis," PLoS One 6(8):e23185, 12 pages (2011).
Martinu et al., "IL-17A contributes to lung fibrosis in a model of chronic pulmonary graft-versus-host disease," Transplantation 103:2264-74 (2019).
Mi et al., "Blocking IL-17A Promotes the Resolution of Pulmonary Inflammation and Fibrosis Via TGF-β1-Dependent and -Independent Mechanisms," J Immunol 187:3003-14 (2011).
Sonnenberg et al., "Pathologic versus protective functions of IL-22 in airway inflammation are regulated by IL-17A," J Exp Med 207:1293-1305 (2010).
Van Dyken et al., "Chitin Activates Parallel Immune Modules that Direct Distinct Inflammatory Responses via Innate Lymphoid Type 2 and γδ T cells," Immunity 40:414-424 (2014).
Wilson et al., "Bleomycin and IL-1β-mediated pulmonary fibrosis is IL-17A dependent," J Exp Med 207:535-552 ( 2010).
Yang et al., "Dysregulated Lung Commensal Bacteria Drive Interleukin-17B Production to Promote Pulmonary Fibrosis through Their Outer Membrane Vesicles," Immunity 50:692-706 (2019).
Zhang et al., "Lack of IL-17 signaling decreases liver fibrosis in murine schistosomiasis japonica," Internat Immunol 27:317-325 (2015).
Barad et al., bioRxiv, posted online on Sep. 8, 2019; doi: http://dx.doi.org/10.1101/762336. (Year: 2019).
Boot et al., J. Bio. Chem., 2001, 276(9): 6770-6778. (Year: 2001).
International Application No. PCT/US2018/027111, International Preliminary Report on Patentability, mailed Oct. 24, 2019.
International Application No. PCT/US2018/027111, International Search Report and Written Opinion, mailed Dec. 4, 2018.
Okawa et al., Loss and Gain of Human Acidic Mammalian Chitinase Activity by Nonsynonymous SNPs, Molecular Biology and Evolution, 33(12):3183-3193 (Oct. 2016).
Reese et al., Chitin induces accumulation in tissue of innate immune cells associated with allergy, Nature, 447:92-96 (May 3, 2007).
Suzuki et al., FEBS Letters, 2001, 506:127-130. (Year: 2001).
Zhang et al., Lack of IL-17 signaling decreases liver fibrosis in murine schistosomiasis japonica, Internal Immunol, 27:317-325 (2015).

* cited by examiner

CHITINASE ADMINISTRATION TO THE AIRWAY TO TREAT INFLAMMATION AND AGE-RELATED PULMONARY FIBROSIS

CROSS REFERENCE TO RELATED APPLICATIONS

This application is a § 371 National Stage Application of International Patent Application Number PCT/US2018/27111, entitled "Chitinase Administration to the Airway to Treat Inflammation and Age-Related Pulmonary Fibrosis," filed on Apr. 11, 2018, which claims priority to U.S. Provisional Patent Application No. 62/484,394, entitled "Chitinase Administration to the Airway to Treat Inflammation and Age-Related Pulmonary Fibrosis," filed on Apr. 11, 2017, each of which is incorporated by reference herein in its entirety.

STATEMENT REGARDING FEDERALLY SPONSORED RESEARCH OR DEVELOPMENT

This invention was made with government support under grant numbers AI030663 and HL128903 awarded by the National Institutes of Health. The government has certain rights in the invention.

BACKGROUND OF THE INVENTION

Pulmonary fibrosis is a chronic, progressive lung disease wherein the alveolar epithelial cells of the lungs become scarred and stiff, resulting in labored breathing, reduced blood oxygen levels, and other morbidities. Certain forms of pulmonary fibrosis, particularly idiopathic pulmonary fibrosis, are incurable and cause or contribute to a substantial number of mortalities each year. There are currently no effective preventative treatments or cures for pulmonary fibrosis, and the cause of the condition is not well understood.

Mucosal barrier dysfunction and immune activation are associated with age-related fibrotic lung diseases, but environmental stimuli that incite these pathways remain largely uncharacterized. The abundant polysaccharide chitin is a rigid, insoluble constituent of fungi, insects, helminths and arthropods. Previous research suggests that chitin is an environmental insult that initiates innate immune cell activation when aspirated into the lung, for example as described in Van Dyken et al. (2014), "Chitin activates parallel immune modules that direct distinct inflammatory responses via innate lymphoid type 2 and γδ T cells," Immunity 40, 414-424.

Mammals express several glycosyl hydrolases, which in mice and humans include enzymatically inactive chi-lectins and two active chitinases, chitotriosidase (Chit1) and acidic mammalian chitinase (AMCase; Chia1), an evolutionarily conserved secreted enzyme that is constitutively expressed in the lung and stomach and is also highly induced during STAT6-dependent immune responses. AMCase was previously proposed to be a driver of reactive airways disease, and treatments that inhibited chitinases in the lungs were proposed as therapeutics for conditions such as asthma (e.g., as described in PCT International Patent Application Publication Number WO2004092404, entitled "Inhibitors of acidic mammalian chitinase as asthma therapeutics," by Folletti) and idiopathic pulmonary fibrosis (e.g., as described in United States Patent Application Publication Number 20130136751, entitled "Methods, compositions and kits relating to chitinases and chitinase-like molecules and inflammatory disease, by Zhu). However, later work suggests that attenuation of chitinase or AMCase activity increases inflammatory cell accumulation and delays resolution after acute chitin challenge (for example, as described in Fitz et al (2012), "Acidic mammalian chitinase is not a critical target for allergic airway disease," Am. J. Respir. Cell Mol. Biol. 46, 71-79.), suggesting an enzymatic role for AMCase in the degradation of insoluble chitin polymers to limit mucosal inflammatory responses in mammals.

However, previously, it has been unknown whether mammalian chitinases such as AMCase and Chit1 function to mediate degradation and facilitate clearance of this ubiquitous insoluble polysaccharide at mucosal barriers under normal physiologic conditions, and whether the activity of native chitinases is relevant to fibrotic lung diseases in humans and other animals.

Accordingly, there remains a need in the art for a deeper understanding of the relationship between environmental chitin and pulmonary fibrosis, and there remains a further need in the art for effective means of preventing and treating the various forms pulmonary fibrosis.

SUMMARY OF THE INVENTION

Provided herein is the first description of spontaneous environmental chitin accumulation in mammalian airways and its association with fibrotic lung disease, as well as the first demonstration that therapeutic delivery of chitinase, even after fibrosis has been established, has a beneficial effect on lung health by reducing spontaneously accumulated chitin as well as inflammatory and fibrotic parameters. The inventors of the present disclosure have advantageously determined that deficits in lung chitinase activity can be an underlying cause of pulmonary fibrosis and other impairments of lung function. The scope of the invention encompasses the novel administration of chitinase to the airway compartments of animal subjects to promote the clearance of environmentally derived chitins. The chitinase is formulated for inhaled delivery, for example in an aerosolized form. Such administration results in the reduction of accumulated chitins in the lungs, reduced inflammatory processes in the lungs, the prevention and treatment of pulmonary fibrosis, and improved pulmonary functions.

The scope of the invention further encompasses novel formulation of chitinases for delivery to the lungs and other airway components, as well as apparatuses for the novel administration of chitinases to the lungs.

The scope of the invention further encompasses novel methods of detecting chitin and chitinase activity as a diagnostic measure of lung health, and for directing treatment to subjects having impaired or inadequate chitinase activity.

These embodiments, and other advantageous discoveries by the inventors of the present disclosure are described in detail below.

BRIEF DESCRIPTION OF THE FIGURES

FIG. 1 depicts chitin amounts in BAL fluid of aged AMCase-deficient control mice (treated with PBS) and aged AMCase-deficient mice treated with exogenous Chit1 (**$p<0.01$ (unpaired t-test), R.U.=relative units).

FIG. 2A depicts survival rates and FIG. 2B depicts hydroxyproline content in lungs of 12-month-old mice: W/T=wild type, C/C=AMCase-knockout, STAT6−/−=STAT6 knockout, and IL4/13−/−=IL4 and IL13 knockout, $p<0.01$; *$p<0.001$ (unpaired t-test).

FIG. 3A: chitin content, as measured by CBD blot, in BAL fluid collected from the lungs of healthy human donors and ILD patients; individuals plotted as single dots; control, n=12; ILD, n=18. FIG. 3B: chitin content in BAL fluid from control mice (WT) and those with conditional deletion of TRF-1 in type II alveolar epithelial cells (TRF-$1^{\Delta\Delta EC2}$); individuals plotted as single dots; n=4-7/group. R.U.=relative units. Lines in represent mean value; p<0.01; *p<0.001 (unpaired t-test), compared to healthy or similarly treated age-matched control.

DETAILED DESCRIPTION OF THE INVENTION

Figure 1:
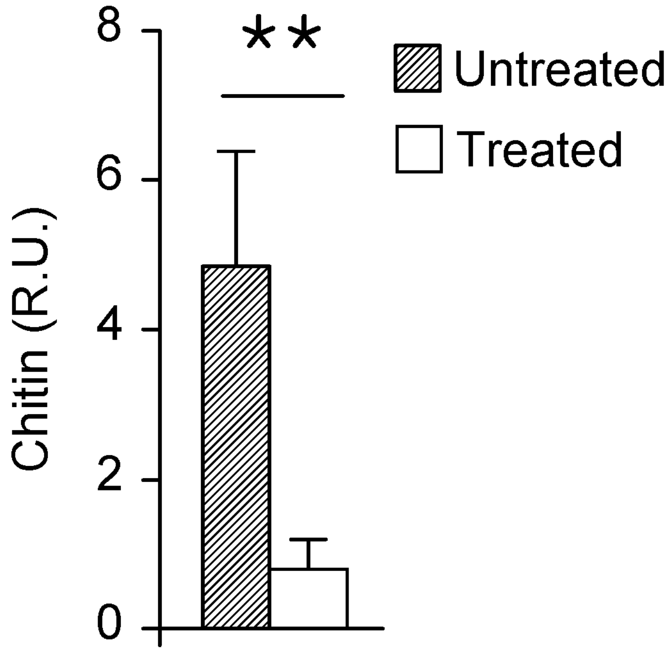
FIG. 1.

General Method of the Invention. The various inventions disclosed herein are based upon the discovery that the accumulation of chitinaceous species in the lung is associated with various pathological processes and conditions, particularly pulmonary fibrosis. The general method of the invention encompasses the administration of chitinases to the lungs or other airway compartments, facilitating the clearance of inhaled chitins and having therapeutic effects against pulmonary fibrosis and lung inflammation, and improving pulmonary function.

Chitinaceous species. Various embodiments are directed to the degradation of chitin oligomers in the airway of an animal. "Chitinaceous species," as used herein, encompasses chitin, being N-acetylglucosamine oligomers of any length and further encompasses any chitin-containing compositions. Chitinaceous species degraded by the methods of the invention may be derived from any source, including from fungal organisms, arthropods, or other organisms.

Chitinases. Various embodiments of the invention are directed to chitinases. A chitinase, as used herein, refers to any enzyme which effects the degradation of chitinaceous species. For example, chitinases, as used herein, encompasses any enzyme which hydrolyzes the glycosidic bonds of chitin oligomers. Chitinases having any form of chitinolytic activity are within the scope of the invention, including endochitinases catalyzing the cleavage of chitin oligomers at internal points of the chitin polymer. Alternatively, the chitinase may comprise an exochitinases which catalyzes the progressive release of acetylchitobiose (chitobiosidase activity) or N-acetylglucosamine (β-N-acetylglucosaminidase) from the ends of the chitin polymer.

Exemplary chitinases include acidic mammalian chitinase (AMCase), including human AMCase and variants. Another exemplary chitinase is chitotriosidase, including human chitotriosidase and variants thereof. "Variants" of an enumerate chitinase, as used herein, refers to compositions structurally similar to the enumerated enzyme, comprising one or more amino acid substitutions, additions, deletions, or fusion partners. The one or more modifications may serve various purposes, for example, increasing the activity of the enzyme, improving the physiological stability of the enzyme, reducing the immunogenicity of the enzyme, or expanding or changing the range of substrates acted upon by the enzyme.

In one embodiment, the chitinase comprises heterologous chitinases, i.e. a non-human chitinase, for example a chitinase from another species or an engineered, non-naturally occurring chitinase. Exemplary heterologous chitinases include those produced by plants or by chitinovorous organisms.

In one implementation, the chitinase comprises an engineered chitinase having higher activity than that of wild-type chitinases. For example, in one embodiment, the chitinases of the invention are chitinases incorporating activity-enhancing mutations. For example, in human AMCase, one or more of the mutations D45, N47, and M61 impart improved chitinase enzymatic activity over wild type N45, D47, and R61, as described in Okawa et al, 2016, "Loss and Gain of Human Acidic Mammalian Chitinase Activity by Nonsynonymous SNPs," Mol. Biol. Evol. 33 (12): 3183-3193.

In one embodiment, the chitinase enzymes of the invention comprise modified enzymes having increased stability, longer half-life, reduced rates of clearance, or which otherwise have improved pharmacokinetic profiles over wild-type enzymes. Exemplary modifications include pegylation and/or glycosylation in the linker region to stabilize the enzyme.

The chitinase may be produced by recombinant means or may be harvested from natural sources. The chitinase may be isolated and purified using any applicable means known in the art.

The various methods of the invention may be described as encompassing the delivery of "a chitinase" to the of the treated subject. It will be understood that such reference encompasses delivery of a therapeutically effective amount of such agent, and is not limited to a single type of agent, i.e. reference to the use of a chitinase may encompass two or more different chitinases used in combination. Therapeutically effective amounts will be any amount that results in the significant degradation and/or clearance of chitin oligomers in the airway of the organism, for example, one or more daily dosages of 10-50 micrograms chitinase per kilogram of body weight.

Subjects. The various methods and agents of the invention are administered to subjects. The subject may be an animal of any species, particularly, a human subject. The subject may also comprise a non-human animal species such as a mouse, rat, dog, cat, pig, cow, horse, non-human primate or any other animal such as a test animal or veterinary subject.

The subject may be in need of treatment for any reason, for example, in need of a therapeutic, restorative, preventative, or other treatment. For example, in one embodiment, the methods and agents of the invention are applied in the treatment chitinase deficiencies, including age-related chitinase deficiencies, or chitinase deficiencies exacerbated or caused by lung dysfunctions or inflammatory conditions. For example, in one embodiment, the methods and agents of the invention are applied to subjects suffering from or at risk of lung pathologies such as fibrotic lung diseases, COPD, asthma, allergies, inflammation, etc. In one embodiment, the subjects may be in need of preventative or prophylactic treatment, for example, being a subject that is exposed to chronic or excessive levels of environmental chitins. In one embodiment, the subject comprises a subject at risk of pulmonary fibrosis due to age, for example, for example a subject of an age of 50 years or older, 55 years or older, 60 years or older, 65 years or older, or 70 years or older.

Target organs and tissues. Various embodiments are described as being applied to the "airway" of a subject. Such reference will encompass any portion of the airway of an animal subject, including the nose and nasal passages, paranasal sinuses, the pharynx, the larynx, trachea, bronchi and bronchioles, and the lungs generally.

Objectives of the Invention. The several methods, agents, and apparatuses described herein may be applied in various contexts, as set forth below.

In a first aspect, the scope of the invention encompasses the reduction of chitinaceous species in the airway of a subject. Such reduction may encompass a reduction in the abundance of chitinaceous species in the lungs or other airway compartments. Such reduction may be manifested as an increase of rate of clearance of chitinaceous species from the airway. Such reduction may encompass an increase in chitinolytic activity in the airway.

In a second aspect, the scope of the invention is directed to the treatment of pulmonary fibrosis. Pulmonary fibrosis, as known in the art, may include any fibrotic lung disease, for example, idiopathic fibrosis, age-related pulmonary fibrosis, environmentally-induced lung fibrosis, and fibrosis occurring as a secondary condition of other lung diseases, e.g. interstitial lung diseases.

"Treatment," as used herein encompasses any therapeutic intervention disclosed herein which prevents, delays, or ameliorates pulmonary fibrosis in any manner. Treatment encompasses interventions which delay the onset of fibrosis in treated subjects, for example, as compared to like untreated subjects. Treatment further encompasses interventions which prevent the occurrence of fibrosis. Treatment may further encompass interventions which slow or arrest the progression of fibrosis. Treatment may further encompass interventions which ameliorate symptoms or severity of fibrosis. Treatment may also encompass interventions which reverse pulmonary fibrosis.

The onset, progression, occurrence, and/or severity of fibrosis addressed by the treatments of the invention may be assessed by any means known in the art. For example, fibrotic lung disease may be assessed by the occurrence or degree of subepithelial collagen deposition, alveolar septal thickening, immune infiltration of lung tissues, parenchymal changes using the Ashcroft scale, elevated levels of hydroxyproline in the lungs, impairments in pulmonary function and performance, and others.

In a third aspect, the scope of the invention encompasses methods of inhibiting one or more physiological processes associated with pulmonary fibrosis. These pathways, enumerated below, are generally related to the immune activation and/or infiltration of cells in the airway which can cause, promote, exacerbate, or otherwise manifest in pulmonary fibrosis and other pathological conditions or processes in the airway. Accordingly, inhibition of any of these physiological processes associated with pulmonary fibrosis may have therapeutic benefits beyond the context of pulmonary fibrosis alone.

Exemplary physiological processes associated with pulmonary fibrosis include persistent epithelial stimulation, accumulation of inflammatory immune cells in airway tissues, the production of pro-fibrotic cytokines, activation of epithelial cell stress pathways, inflammatory immune signaling, and dysregulation of homeostatic barrier functions. For example, physiological processes include inducement of or infiltration by group 2 innate lymphoid cells (ILC2s), IL-17A-producing γδ T cells, other γδ T cells, CD4+ T cells, eosinophils, and neutrophils. Other exemplary pathways induced, exacerbated, or associated with chitin accumulation include NRF2-mediated oxidative stress responses, unfolded protein responses (Xbp1, Atf4), NF-kB signaling (Il33, Nfkbib), and telomerase signaling (Hsp90aa1, Myc).

In a fourth aspect, the scope of the invention is directed to methods of enhancing pulmonary function. Enhancement of pulmonary function encompasses any improvement or stabilization of lung functions or performance, as assessed by any measure known in the art. Exemplary measures of pulmonary performance include assessment of blood oxygen saturation, spirometry measurements, plethysmography, and other assessments of pulmonary or lung function known in the art.

Uses of Chitinases. In a first aspect, the scope of the invention encompasses a chitinase for use in the degradation chitin oligomers in the airway of a subject. In another aspect, the scope of the invention encompasses a chitinase for use in a method of treating pulmonary fibrosis. In another aspect, the scope of the invention encompasses a chitinase for use in the inhibition of a physiological process implicated in pulmonary fibrosis. In another aspect, the scope of the invention encompasses a chitinase for enhancing pulmonary function.

In yet another aspect, the scope of the invention encompasses the use of a chitinase in the manufacture of a medicament for the degradation of chitin oligomers in the airway of subject. In another aspect, the scope of the invention encompasses the use of a chitinase in the manufacture of a medicament for the treatment of pulmonary fibrosis. In another aspect, the scope of the invention encompasses the use of a chitinase in the manufacture of a medicament for the inhibition of a physiological process associated with pulmonary fibrosis. In another aspect, the scope of the invention encompasses the use of a chitinase in the manufacture of a medicament for enhancing pulmonary function in a subject.

In one aspect, the scope of the invention encompasses a method of degrading chitin oligomers in the airway of a subject by the administration to the airway of the subject of a pharmaceutically effective amount of a chitinase. In one aspect, the scope of the invention encompasses a method of treating pulmonary fibrosis in a subject in need of treatment therefor by the administration of a pharmaceutically effective amount of a chitinase to the airway of the subject. In one aspect, the scope of the invention encompasses a method of inhibiting a pathway or physiological process implicated in pulmonary fibrosis in a subject by the administration of a pharmaceutically effective amount of a chitinase. In one aspect, the scope of the invention encompasses a method of improving pulmonary function in a subject in need of such improvement by the administration of a pharmaceutically effective amount of a chitinase.

Non-Chitinolytic Agents and Enhancement of Lung Chitinolytic Activity. The various embodiments of the invention described above are directed to the use of chitinases. However, it will be understood that the scope of the invention encompasses any treatment or agent which enhances the clearance of chitin oligomers from the lungs or which inhibits the pathogenic properties of chitinaceous species inhaled to the lung.

Accordingly, in an alternative implementation, the scope of the invention encompasses the delivery of an agent that does not have chitinolytic activity, but which acts by other means to deactivate, remove, degrade, or otherwise reduce the abundance of or pathogenic biological activity of chitin species within the respiratory tract.

In one implementation, the agent of the invention comprises a composition of matter which increases, restores, or maintains chitinase activity in the respiratory tract of a treated subject.

In one implementation, the agent comprises an agent that induces the expression of functional chitinases by cells within the subject's respiratory tract. In such implementation, the agents of the invention encompass gene therapy constructs for transforming lung epithelial or other cells to enhance their chitinase expression. In this implementation, the agents may comprise gene therapy vectors that are delivered to the respiratory tract and which transform extant cells and cause them to produce one or more chitinases.

In another implementation, the agents of the invention comprise cell therapy vectors, which, upon administration to the airway of the subject, increase the population of chitinase-secreting cells. In such methods, cells, such as autologous cells or allogenic cells are engineered to express one or more chitinases. The cells may comprise lung epithelial cells, multipotent epithelial stem cells, or other lung cells or lung cell precursors known in the art. Such cells are then administered to the respiratory tract of the patient where they are incorporated into extant lung tissue, for example by differentiation of lung cell precursors. The newly incorporated cells produce chitinases to augment or restore endogenous chitinase production.

Delivery methods and Devices. The several uses and methods of the invention encompass the administration of chitinases to airway tissues and compartments to promote the inactivation, destruction, or clearance of accumulated or inhaled chitins. Accordingly, in many implementations, the delivery may comprise the delivery of an aerosolized chitinase to the target tissues of the subject. The scope of the invention encompasses such methods of aerosolized delivery as well as the devices utilized for such delivery.

Chitinase is a fairly robust and stable enzyme, is not membrane bound, is not overly hydrophobic, hydrophilic, or charged. Accordingly, chitinases are amenable to known methods of delivering enzymes and other biologicals to the lungs. Chitinase delivery to the lungs may be accomplished by the use of methods, formulations, and devices known in the art, for example, as described in PCT Patent Application Publication Number WO2002043695, entitled “Stable, aerosolizable suspensions of proteins,” by Cowan; U.S. Pat. No. 5,618,786, entitled “Aerosolization of protein therapeutic agent,” by Roosdorp et al.; and U.S. Pat. No. 9,554,993, entitled “Pulmonary delivery particles comprising an active agent,” by Tarara et al.

The scope of the invention further encompasses formulations of chitinases for aerosolized delivery to the airway. The formulation may be prepared as known in the art of drug delivery. The formulation may comprise one or more excipients that improve the stabilization, aerosolization, dispersal, adsorption/absorption, or other delivery parameters of the chitinase. For example, therapeutic proteins delivered by the pulmonary route are typically combined with surfactants that mediate adsorption or absorption of the delivered enzyme to lung epithelial surfaces. The one or more agents, such as chitinases, to be delivered in the formulation may be encased within polymeric nanoparticles, liposomes, or other drug delivery vehicles. Formulations may comprise dry powders or may comprise liquid formulations such as suspensions, emulsions, or solutions. Powdered enzymes may be spray dried, lyophilized, or otherwise prepared, and may comprise particulates of an effectively respirable size, for example, in the range of 1 μm to 5 μm.

The scope of the invention encompasses apparatuses for the delivery of the agent to the airway of the subject. Such devices will comprise an apparatus which holds the selected chitinase and which is capable of delivering a controlled dosage of such chitinase to the airway tissues of the subject. The delivery may be accomplished by pumps, vaporizing elements such as heaters or vibrational energy sources, or by the use of compressed gases and propellants, as known in the art.

In one embodiment, the device comprises a dry powder inhaler. In one embodiment, the device comprises a metered-dose inhaler. In one embodiment, the device comprises a nebulizer.

Chitinase Diagnostic Methods. As disclosed herein, the inventors of the present disclosure have newly determined that chitinase activity is essential for lung health and is implicated in lung pathologies such as pulmonary fibrosis. Accordingly, assessment of lung chitinase activity may serve as a novel diagnostic measure of pulmonary fibrosis, associated inflammatory processes, and overall lung health.

In one aspect, the scope of the invention is broadly directed to methods of assessing lung chitinolytic activity in a subject. In one embodiment, the invention comprises a diagnostic method of assessing a chitinolytic deficiency in a subject. A “chitinolytic deficiency,” as used herein, is any suboptimal level of chitinolytic activity in the airway of the subject. In one aspect, the chitinolytic deficiency represents impaired chitinolytic activity, wherein the subject’s ability to clear chitin from the lungs is diminished, compared to that in healthy subjects, for example, due to factors such as age, inflammation, pulmonary fibrosis, or other pulmonary disease or condition. In another aspect, the chitinolytic deficiency is related to excessive chitin exposure, i.e. the subject may have at least normal levels of chitinolytic activity in their lungs, however the level of activity is not sufficient to keep the airway clear of pathological chitins due to excessive exposure.

The general diagnostic method of determining a chitinase deficiency in a subject comprises the steps as follows:

- a measure of chitinolytic activity is selected;
- a representative sample is collected from a subject;
- chitinolytic activity is determined by assessing the selected measure of chitinolytic activity in the sample;
- the measured value of chitinolytic activity is compared against a threshold value, scale, index, or other range of values that define healthy and deficient chitinolytic activity levels, wherein the subject is deemed to have a chitinolytic deficiency if the measured value is within a range of values defining chitinolytic deficiency.

The representative sample may comprise any tissue, exudate, or other biological sample derived from the subject which is amenable to assaying for the selected measure of chitinolytic activity. The sample may comprise any lung tissue or exudate material, including bronchalveoar lavage fluid, droplets isolated from exhaled air, sputum lung swabs, lung tissue biopsies, and other lung sample types known in the art. Other samples may include serum, nasal swabs, and saliva.

In one embodiment, the selected measure of chitinolytic activity is a measurement of chitin abundance in the lungs or respiratory tract. Such quantification of chitinaceous species may be achieved by any appropriate assay. In one embodiment, chitin abundance is determined by mass spectroscopy. In one embodiment, a probe such as a labeled antibody or other chitin-binding composition is applied to the sample and the abundance of the label is used as a measure of chitin abundance. Exemplary chitin probes include compositions described in U.S. Pat. No. 9,516,879, entitled “Chitinous polysaccharide antigen-binding proteins,” to Verheesen et al. and PCT International Patent Application Publication Number WO199046390, entitled “Chitinase chitin binding fragments,” to Gray and Tjolker. In one embodiment, the assay utilizes a fluorescein-tagged chitin binding domain protein, comprising any of several known peptide sequences which can selectively bind to motifs present in chitinaceous species, such as that described in Kabir et al. (2012), entitled “Fluorescein-5 isothiocyanate conjugated-chitin-binding domain probe (FITC-CBD)-coupled detection of chitin in the peritrophic membrane of *Monochamus alternatus* (Coleoptera: Cerambycidae)," Journal of Asia-Pacific Entomology 15:397-400.

In one embodiment, the measure of chitinolytic activity comprises a measurement of chitinase enzymatic activity in the sample. Such assessment may be achieved using methods known in the art, for example by the use of chitinaceous substrates that yield detectable end products upon enzymatic cleavage, for example, substrates that release p-nitrophenol, which upon ionization in basic pH, can be measured colorimetrically. Exemplary assays include those described in: Wirth and Wolf (1990), entitled "Dye-labelled substrates for the assay and detection of chitinase and lysozyme activity," Journal of Microbiological Methods 12:197-205 and Ferrari et al. (2014), entitled "A fast, sensitive and easy colorimetric assay for chitinase and cellulase activity detection," *Biotechnology for Biofuels* 7:37. In an alternative implementation, chitinase activity is estimated by quantifying chitinase enzyme abundance, for example by the use of labeled antibodies to lung chitinases, e.g., AMCase.

The measurement of chitinolyitc activity attained for the sample is then compared against a selected threshold value, scale, index, or other set of one or more values indicative of healthy and deficient chitinolytic activity. Such threshold value, scale, index, or other set of one or more values may be established, for example in appropriately matched (e.g. by demographic factors, disease status, age, etc.) subjects comprising healthy and unhealthy subjects, using like samples. In one embodiment, the measured value of chitinolytic activity is compared against an index comprising a probability index, wherein the subject's risk of a condition such as pulmonary fibrosis is determined.

In one embodiment, a chitinase deficiency is assessed when a subject has measured chitinolytic activity which is at a value less than two standard deviations below that found in persons without disease, for example, subjects of the same age, or for example, when observed in the presence of lung function compromise consistent with chronic fibrosing or inflammatory injury. In another embodiment, chitinolytic deficiency is defined as the abundance in the subject of detectable chitin species at a value above two standard deviations of that measured in persons without disease.

Establishment of a chitinolytic deficiency in the subject may be used to diagnose an associated condition, such as: an overexposure to environmental chitins (e.g. in the context of air quality or workplace safety); an inability to effectively clear inhaled chitinaceous materials from the lungs; an impaired chitinase-producing capability; the risk or presence of lung inflammation; the risk or presence of pulmonary fibrosis; and a need for the administration of exogenous chitinase.

In a further implementation, the scope of the invention comprises a method of treating a subject for a condition selected from the following: exposure to excessive environmental chitin, accumulation of pathological levels of chitin in the airway; pathological lung inflammation; pulmonary fibrosis, and impaired pulmonary function. In this method, the general diagnostic method above is applied, followed by administration of a treatment if a chitinase deficiency is established. The treatment may be administration of chitinase to the airway of the subject. The treatment may alternatively comprise a mitigation of the chitin exposure of the subject.

In another implementation, a putative treatment to increase chitinolytic activity is applied to an animal, and chitinolytic activity is measured against previous measurements from the same animal or against untreated control levels in order to determine the efficacy of the treatment. In another embodiment, chitinolytic activity is measured in a patient receiving a chitinolytic-enhancing treatment and the resulting measurement is used to determine the efficacy of the treatment for that patient.

EXAMPLES. Given the widespread distribution of chitin substrates in the environment, experiments were conducted to determine whether mammalian chitinases such as AMCase and Chit1 function to mediate degradation and facilitate clearance of this ubiquitous insoluble polysaccharide at mucosal barriers under normal physiologic conditions, and to determine the significance of airway chitinase activity for lung and general health.

Example 1. Airway endochitinase activity is mediated by AMCase-expressing epithelial cells. An AMCase fused to a fluorescent reporter was introduced into mice. Among CD45-lung cells, a population of AMCase-expressing was observed. comprising a subset of secretory lung epithelial cells including club cells and type 2 alveolar cells lining proximal and distal airways. Lung AMCase mRNA was absent in homozygous knockout mice, while expression of chi-lectins remained normal, and chitotriosidase (Chit1), was not detected in lung tissue from wild-type, AMCase transgenic or AMCase-deficient mice. AMCase, protein was readily detected in bronchoalveolar lavage (BAL) fluid of wild-type mice but absent in homozygous knockout mice.

Example 2. Constitutive AMCase expression is independent of type 2 cytokine signaling. The type 2 cytokines IL-4 and IL-13, along with their shared signaling adapter STAT6, are known to mediate AMCase induction in the lungs following type 2 immune challenges such as allergens and helminths. The response of the reporter allele to exogenous type 2 cytokine stimulation was assessed by administrating IL-13 into the airways of heterozygous mice. This treatment increased both the percentage of epithelial cells that expressed the reporter and the median fluorescence intensity among reporter-expressing cells. Airway chitinase activity in the steady-state, however, was not dependent on either STAT6 or IL-4/13, and endochitinase activity in BAL fluid was normal in mice with genetic deficiencies in either STAT6 or IL-4/13 and constitutive reporter expression in these cells remained normal in the absence of type 2 cytokine signaling, indicating that the reporter accurately reflects AMCase activity.

Example 3. Constitutive AMCase maintains lifespan and lung health with aging. A spontaneous progressive health decline was observed in a significant proportion of aging AMCase-deficient mice housed in standard barrier conditions, variably characterized by hunched posture, labored breathing, poor grooming/hair loss, skin lesions, and death. In 12-month-old AMCase-deficient mice, oxygen saturation levels were significantly lower than in similarly aged wild-type controls, consistent with impaired lung function. Analysis of lung tissue from 6-9 month-old AMCase-deficient mice revealed a pleomorphic accumulation of inflammatory immune cells, including group 2 innate lymphoid cells (ILC2s), γδ T cells, CD4+ T cells, eosinophils, and neutrophils, which resembled the profile of the lung cellular infiltrate induced after acute inhalation of purified chitin in wild-type mice in previous reports.

Example 4. AMCase-deficient mice develop spontaneous age-related lung fibrosis. Activation of resident lung ILC2s and γδ T cells after chitin inhalation is known to induce IL-13 and IL-17A production from these cells, which cytokines have previously been implicated in the pathogenesis of lung fibrosis. AMCase-deficient mice were bred onto IFNγ/IL-17A/IL-5/IL-13 cytokine reporter to assess the spontaneous expression of these cytokines among resident lung lymphocyte populations. Significantly increased percentages of lymphoid cells expressing these cytokines among CD4+ T cells, γδ T cells, and ILC2s were observed in the lungs of AMCase-deficient mice as compared to wild-type controls. Cytokine-expressing cells became more pronounced with age, suggesting a persistent cytokine-mediated immune stimulation contributed to chronic tissue alterations. AMCase-deficient mice spontaneously developed age-related lung fibrosis, evidenced by increased subepithelial collagen deposition that was most prominent around conducting airways and vasculature, alveolar septal thickening and infiltration and higher fibrosis scores as assessed by parenchymal changes using the Ashcroft scale, as well as significantly increased lung hydroxyproline levels, and a dysregulated immune responses to helminth infection, consistent with systemic inflammation Example 5. Chitin accumulates spontaneously in the airways of aged AMCase-deficient mice and contributes to fibrosis. Chitinase activity in the BAL fluid of AMCase-deficient animals remained undetectable with age. BAL fluid isolated from AMCase-deficient mice at ages corresponding with fibrosis contained significantly elevated levels of spontaneously acquired chitin fragments than did wild-type controls, as assessed using a highly-specific chitin-binding-domain (CBD)-containing probe. These chitin fragments likely derived from sources in the immediate environment of the mice. Extracts of house dust mite (*Dermatophagoides farinae*) and mold (*Aspergillus niger*), each of which contains chitin elements sensitive to chitinase degradation, were administered to wild-type and AMCase-deficient mice. At times when wild-type mice resolved inflammation, AMCase-deficient mice retained significant accumulations of γδ T cells, CD4+ T cells, neutrophils and eosinophils, showing AMCase activity is inversely related to chitin levels and lung inflammation delayed resolution due to altered chitin clearance. Depletion of chitin from *A. niger* by pre-treatment with active chitinase reduced total BAL chitin levels in AMCase-deficient animals after challenge, restoring the resolution of inflammation while challenge with purified chitin led to increased accumulation of γδ T cells and neutrophils in the lungs of AMCase-deficient mice Higher numbers of lung ILC2s, γδ T cells and IL-17A-producing γδ T cells were observed in AMCase-deficient mice throughout the enhanced response to *A. niger*, consistent with increased activation of lymphoid cell populations and production of pro-fibrotic cytokines by persistent chitin-mediated injury.

Mice with lung-specific (surfactant protein C promoter-driven) transgenic expression of AMCase on a ChiaRed AMCase reporter homozygous background (SPAM×CC) were generated. BAL chitobiosidase activity was robustly restored in SPAM×CC mice, to levels approximately 10-fold higher than in BAL collected from wild-type animals. This restoration significantly reduced the levels of chitin polymers in the airways of 9-month-old SPAM×CC mice compared to co-housed littermate CC mice. Remarkably, lung-specific transgenic AMCase restoration also ameliorated the inflammatory infiltrates and fibrosis in aged CC mice, consistent with a role for AMCase in mediating homeostatic degradation and turnover of immunostimulatory environmental chitin. To additionally test whether restoration of chitinase enzymatic activity was sufficient to ameliorate disease, recombinant chitotriosidase (Chit1) was instilled into the airways of aged AMCase-deficient mice repeatedly for 3 weeks. Mice, (average mass 30 grams), had 1 microgram of Chit1 in 40 microliters PBS intranasally instilled every 2 days for 20 days. This regimen significantly elevated airway chitobiosidase activity for 48 hours after each dose, although this level remained below that of wild-type mice. In agreement with the genetic chitinase restoration, treatment with Chit1 significantly reduced chitin polymer accumulation in the BAL of aged AMCase-deficient mice (FIG. 1), along with percentages of cytokine-expressing lymphoid cells, particularly IL-17-expressing CD4+ T cells and γδ T cells, as well as IL-13-expressing ILC2s in the lungs of AMCase-deficient mice as compared to wild-type controls. Furthermore, a significant reduction in the hydroxyproline content of the lungs treated with Chit1 was observed as compared to PBS, showing that abnormal chitin accumulation contributed to pro-fibrotic cytokine production and the severity of fibrosis, which was responsive to enzyme replacement therapy in the context of AMCase deficiency and aging.

Example 6. Cytokine signaling and cellular stress pathways induced in AMCase-deficient epithelium. Homeostatic maintenance of the airways requires anticipatory production of enzymes, scavengers, and other factors moderating cellular stress pathways in response to periodic environmental insults, including exposures to pollutants, toxins, particulates, and endogenously produced reactive metabolites. The abnormal accumulation of chitin particles and the development of fibrosis in aged AMCase-deficient mice demonstrated that disease was initiated by epithelial dysfunction. RNA-Seq was performed to compare the transcriptomes of ChiaRed reporter-positive epithelial cells isolated from the lungs of 12-week-old heterozygous and homozygous mice, prior to the onset of lung fibrosis. 1463 genes were differentially expressed between C/+ and C/C epithelial cells, indicating broad transcriptomic changes in the absence of AMCase. Pathway analysis indicated significant alterations between AMCase-deficient homozygous and heterozygous ChiaRed+epithelial cells in a wide array of canonical pathways, including those involved in maintaining cellular integrity and cytokine signaling, revealing the induction of these pathways prior to the onset of fibrotic disease in AMCase-deficient animals: Gene sets belonging to pathways including NRF2-mediated oxidative stress responses (e.g., Nfe212, Fos, Actb, Maff), unfolded protein responses (Xbp1, Atf4), NF-kB signaling (Il33, Nfkbib), telomerase signaling (Hsp90aa1, Myc), and circadian rhythms (Per1, Per2, Cry1, Cry2) were statistically overrepresented in AMCase-deficient cells as compared to heterozygous cells. These results demonstrate that the inability to efficiently clear chitin particles from the airways initiates activation of epithelial cell stress pathways, inflammatory immune signaling and dysregulation of homeostatic barrier function, which processes have previously been implicated in the development of lung fibrosis.

Figure 2A:
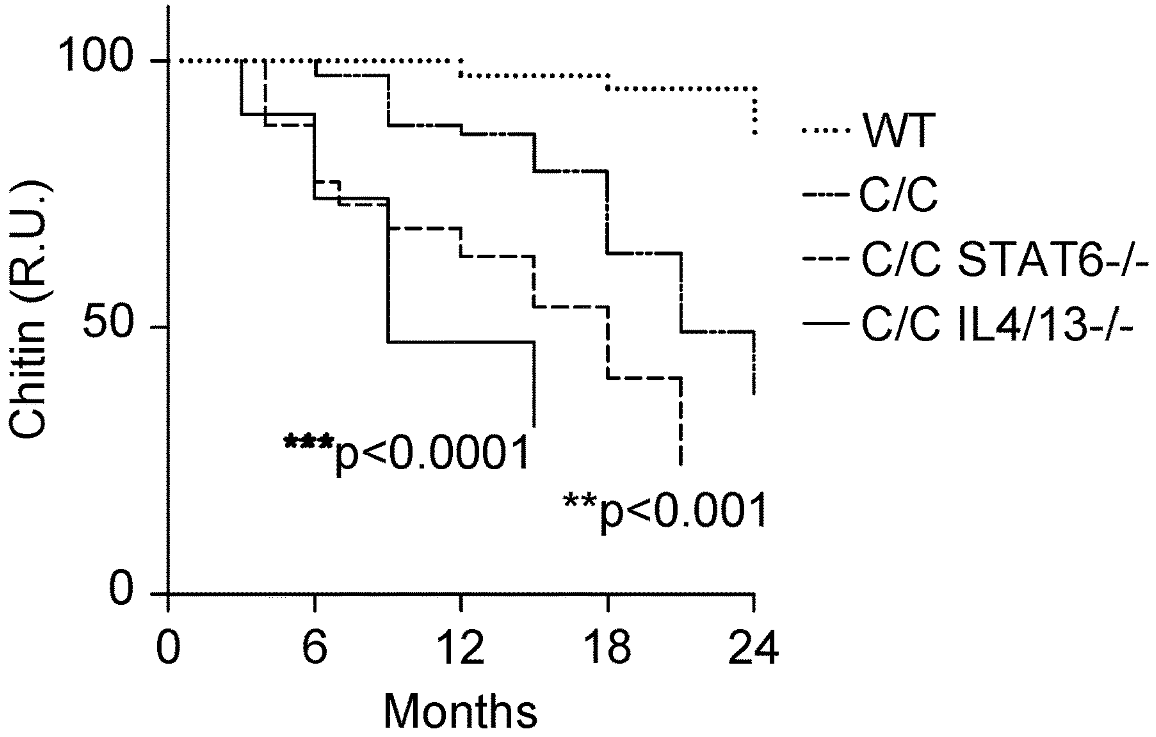
FIGS. 2A and 2B.
Figure 2B:
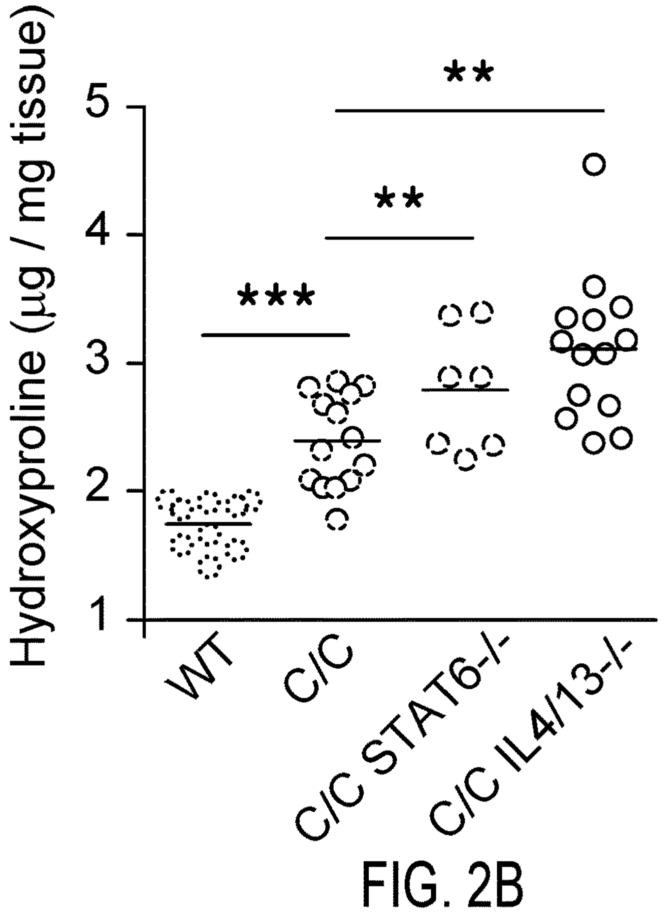

IL-5 deficiency eliminated the lung eosinophil accumulation in aged CC animals, this reduction had no effect on the lung fibrosis as measured by hydroxyproline content In contrast, loss of IL-4 and IL-13 or their signaling adapter STAT6 profoundly exacerbated fibrotic lung disease and death rates in aging CC animals (FIGS. 2A and 2B), demonstrating that certain type 2 cytokine-mediated pathways protect against severe lung injury, enhanced fibrosis, and death in the context of AMCase deficiency.

Figure 3A:
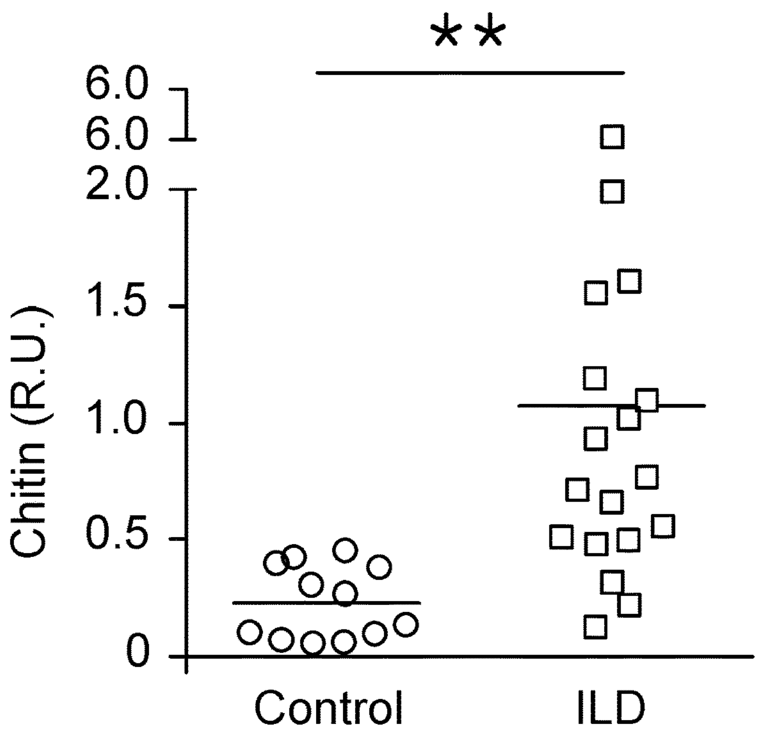
FIGS. 3A and 3B.
Figure 3B:
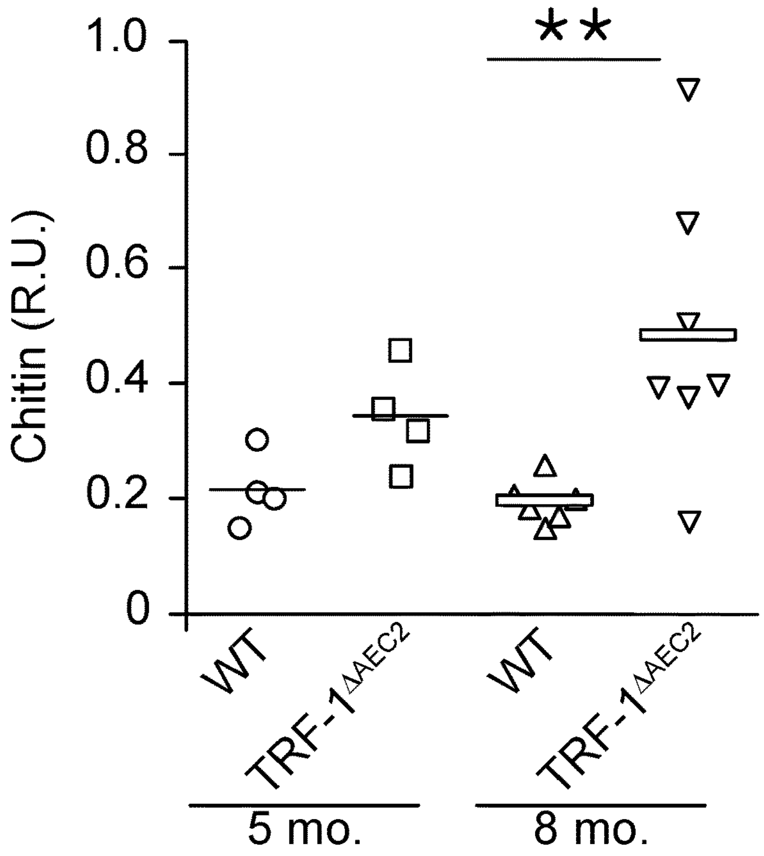

Example 7. Human ILD patients accumulate chitin polymers in BAL fluid. Age-related pulmonary fibrosis in humans has previously been associated with chronic exposure to insoluble particles, such as asbestos, silica and beryllium. Here, AMCase protein was readily detected in BAL fluid from healthy human controls and patients with interstitial lung disease [ILD; comprising idiopathic pulmonary fibrosis (IPF) or pulmonary fibrosis associated with scleroderma] or asthma, while chitotriosidase, was not prevalent. No difference in AMCase protein levels were detected in BAL fluid between controls and patients with ILD or asthma. As assessed using CBD-reactive material, significantly increased amounts of chitin polymers were present in BAL fluid from patients with ILD as compared to healthy controls (FIG. 3A). This accumulation of chitin polymers was significant in patients with either IPF or pulmonary fibrosis associated with scleroderma and did not appear to be a generalized feature of lung inflammatory disorders, since the low level of chitin in the BAL fluid from patients with asthma did not differ from healthy controls. Similarly, mice that develop pulmonary fibrosis due to the conditional deletion of the protective telomere factor TRF-1 in alveolar type II cells) also accumulated chitin polymers in the airways with age (FIG. 3B), indicating that induction of epithelial dysfunction alone was sufficient to impair chitin clearance from the airways. These data demonstrate that physiologic control of environmental chitin is not maintained in the setting of abnormal fibrotic lung architecture and aging, reflecting impaired mucociliary clearance, cellular stress, or epithelial dysfunction in combination with low AMCase activity, or the inability to induce endochitinase production to high levels similar to those invoked by robust type 2 immunity and STAT6-mediated repair pathways.

Summarizing, the foregoing Examples show that AMCase is a constitutively secreted and non-redundant enzyme that mediates the clearance of environmental chitin from healthy airways. In its absence, significant morbidity and mortality occurs in mice associated with accumulation of chitin polymers and persistent activation of immune cells and cytokines previously implicated in low-grade inflammation and fibrosis. Reducing airway chitinase activity in mice alters the normal resolution of inflammation following challenge with complex biologic chitin-containing constituents, implicating a contributory inflammatory role for chitin. The results suggest that chitin degradation by chitinase is a constitutive and essential process that maintains lung homeostasis, since aged AMCase-deficient mice developed spontaneous lung fibrosis in association with activated cytokine and molecular pathways previously implicated in this process. Therapeutic administration of exogeneous chitinase to the airways reduced fibrosis in aged animals, showing that restoring the ability to clear or degrade naturally-acquired chitin particles can ameliorate persistent stimulation of innate inflammatory pathways associated with chitin particle accumulation and lung disease.

The results show that specialized AMCase-expressing lung epithelial cells, as revealed by the AMCase reporter mouse, are critical in mediating the degradation and clearance of the stimulus and thereby act as negative regulators of the persistent inflammatory pathways that mirror the pattern of cell and cytokine activation triggered by experimental acute chitin exposure in wild-type mice. Replacement of chitinase activity by Chit1 administration to the airways of AMCase-deficient mice was sufficient to reduce chitin levels, ameliorate cytokine expression, and lessen fibrosis, highlighting the essential role for this specific enzymatic activity in the airways. Notably, similar patterns of inflammation to those induced by chitin occur in response to an array of lung epithelial tissue perturbations containing chitin, including helminth infection, dust mite, protease and fungal exposures and may contribute to lung fibrosis when dysregulated. These stereotyped cytokine networks in response to lung injury appear to connect general pathways of epithelial dysfunction (oxidative stress, activation of UPR, periodic cycling) with tissue inflammation that, in the case of AMCase deficiency, can be exacerbated by accumulation of particles normally cleared through enzymatic degradation. A complex interplay between the epithelium and associated cytokines, however, was revealed by the exacerbation of the AMCase-deficiency phenotype in the absence of IL-4/IL-13 signaling, indicting that protective factors are simultaneously engaged in the context of immune stimulation.

Although AMCase expression in the steady-state is required to prevent spontaneous disease associated with accumulation of chitin polymers, low levels of AMCase expression or activity in the context of fibrosis or aging appear unable to mediate efficient chitin clearance or degradation, as suggested by lower levels of chitin accumulation in airways of aged wild-type mice and the inability to clear chitin in the context of human ILD and mice with telomere dysfunction. In the latter cases, chitin may be an environmental driver that contributes to the exacerbation of underlying disease induced by epithelial dysregulation. Intriguingly, lung fibrosis due to AMCase deficiency appears to initially activate gene pathways mediating epithelial integrity that have been previously implicated in the setting of lung fibrosis, showing that abnormal retention of chitin polymers in the airways instigates common epithelial stress pathways.

The findings that AMCase is the predominant chitinase in human BAL fluid and that chitin polymers accumulate in the lungs of patients with ILD demonstrate that chitin constitutes an environmental driver that contributes to the progression of lung diseases of diverse etiologies as normal epithelial function becomes compromised with age.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of preventing or treating pulmonary fibrosis in a subject by degrading inhaled chitin oligomers in the airway of the subject; comprising administering to the airway of the subject a pharmaceutically effective amount of a chitinase.

2. The method of claim 1, wherein the subject is suffering from pulmonary fibrosis.

3. The method of claim 1, wherein the chitinase is AMCase.

4. The method of claim 1, wherein the chitinase is chitotriosidase.

5. The method of claim 4, wherein the administration is a preventative treatment; wherein the subject is at risk of pulmonary fibrosis.

6. The method of claim 5, wherein the subject is of age fifty years or older.

* * * * *